United States Patent
Baege et al.

[11] Patent Number: 5,965,006
[45] Date of Patent: Oct. 12, 1999

[54] METHOD FOR PRODUCING A METAL SURFACE

[75] Inventors: Roland Baege, Wiesendangen, Switzerland; John Maclaren Cassells, Houghton, United Kingdom; Toby StJohn King, Cambridge, United Kingdom; Timothy Andrew Large, Cambs, United Kingdom; Anne Tregoning Miller, Cambridge, United Kingdom

[73] Assignee: Sulzer Orthopaedie AG, Baar, Sweden

[21] Appl. No.: 08/803,885

[22] Filed: Feb. 20, 1997

[30] Foreign Application Priority Data

Apr. 10, 1996 [EP] European Pat. Off. ............. 96810221

[51] Int. Cl.⁶ ........................................................ C25F 3/02
[52] U.S. Cl. .......................... 205/666; 205/674; 205/685
[58] Field of Search .................................... 205/655, 665, 205/666, 667, 674, 685, 223, 224

[56] References Cited

U.S. PATENT DOCUMENTS

| | | |
|---|---|---|
| 3,359,192 | 12/1967 | Heinrich et al. ............... 205/665 X |
| 5,246,530 | 9/1993 | Bugle . |
| 5,258,098 | 11/1993 | Wagner . |
| 5,344,458 | 9/1994 | Bonutti . |
| 5,766,238 | 6/1998 | Lau et al. ........................... 205/640 X |

FOREIGN PATENT DOCUMENTS

| | | |
|---|---|---|
| 0 373 011 | 6/1990 | European Pat. Off. . |
| 0 540 290 A3 | 5/1993 | European Pat. Off. . |
| 2169945 | 9/1973 | France . |
| 31 19130 A1 | 3/1983 | Germany . |

*Primary Examiner*—Donald R. Valentine
*Attorney, Agent, or Firm*—Townsend and Townsend and Crew LLP

[57] ABSTRACT

The invention shows a surface (2) for a metal implant (1) which has a coarse structure of elevations (3) and depressions (4), with the surface (2) being permeated by a network (5) of protruding ribs which form nodes (7) and interstices or meshes (8) having an interstice width of 2 mm to 0.4 mm, while the depressions represent sections of spherical cavities (11). The nodes (7) of the ribs can protrude the furthest like mountain peaks, whereas the ribs (6) which connect two nodes (7) each form a lower lying saddle (10) if the spherical cavities penetrate one another slightly. Through coating with an electrochemically resistant protective lacquer, into which holes can be shot at a predetermined spacing without damaging the metal, with a laser for example, a coarsely structured intermediary surface can be economically provided by means of electrochemical erosion which receives a fine structure through sand blasting.

17 Claims, 10 Drawing Sheets

METHOD FOR PRODUCING A METAL SURFACE

BACKGROUND OF THE INVENTION

The invention relates to a metal implant, by way of example for bones, the implant having a surface with a coarse structure of elevations and depressions, and to methods for producing the surface.

U.S. Pat. No. 4,673,409 and the U.S. Pat. No. 4,608,052 show a surface in which, starting from a smooth metal surface, pillars are produced by the material in that a laser is used to liquefy and vaporize material around the pillars in the form of channels of cylindrical blind holes placed adjacent to one another in a row. The upper faces of these pillars, which lie in the originally smooth metal surface, form support surfaces for a primary anchoring in the bone tissue; and the hollow spaces surrounding them can accommodate bone tissue that grows in later or bone cement. This type of metal processing is enormously complicated and expensive since the excess material must be vaporized at the low efficiency of a laser and since the focal point of the laser optics must continually be adjusted very precisely in its distance to the surface. Furthermore, during the spontaneous melting and vaporization, metal sprays arise which are in no regard desirable so that U.S. Pat. No. 5,264,530 proposes to apply a protective coating prior to the laser drilling which can later be removed and which is also bored through and which prevents liquid metal sprays from striking the surface that it covers. Solvent soluble binders with metallic oxides which are heat resistant at high temperatures are considered as typical protective coatings. Nevertheless it is, of course, not possible to prevent metal sprays being deposited in the already cut channels.

SUMMARY OF THE INVENTION

It is an object of the invention to provide surfaces for a good anchoring of a metal implant and simultaneously to develop methods which permit a rational manufacture of such surfaces.

This object is attained by permeating the surface with a network of protruding ribs which form nodes and interstices or meshes having an interstice width of 2 mm to 0.4 mm, by the interstices each forming a recess in the form of a section of a spherical cavity, and by the coarse structure having a fine structure for the anchoring.

A surface of this kind has the advantage that a network of ribs is available for the primary anchoring whose edges can take up shear forces at the spherical cavities independently of the direction, and the edges of which, as a sum, have an enormous length for taking up shear forces due to the small dimensions and due to the dense arrangement of the round cavities. The depth of a round cavity, which can grow to a bit more than the radius of a hemispherical shell, is provided as the anchoring depth for ingrowing bone matter.

For the primary anchoring of non-cemented prostheses, a bone bed is hollowed out in a bone which corresponds to a slightly reduced envelope surface at the surface of the prosthesis. In such a case it continues to be advantageous for the primary anchoring if the ribs form a saddle between two nodes, since the round cavities partially penetrate one another at their edges. With such an arrangement it is ensured that, when the normal force between the surface and the bone matter increases, first the edges at the nodes and then the edges at the saddle points penetrate into the bone matter and form a support surface which rapidly increases with the penetration depth, which does not lie in the envelope of the surface and which prevents sliding. If the indentation V of the saddle points with respect to the nodes amounts to 0<V<50% of the depth of the round cavities, then a perforation of the bone structure by individual pillars can be avoided and a pronounced upper surface acting as a sliding surface and coinciding with an envelope can be avoided. A surface of this kind is particularly suitable as a direct anchorage for an implant in bones if it consists of body-compatible material such as titanium or titanium alloys, for example. In metals such as, for example cobalt-chromium alloys, this surface can be used for an anchoring in bone cement. Through the network-shaped arrangement of the ribs and through the enlargement of their cross-section at increasing depth, filigree interstices with an interstice width down to 0.4 mm can be used even in the relatively soft pure titanium.

The spherical cavities can be arranged with their midpoints at spacings which correspond to a grid. This is, however, not obligatory. Since even the mixed form with narrow ribs without saddle points and with ribs with saddle points is suitable as a coarse structure, the spherical cavities may also intersect insubstantially or just fail to intersect in a "wild" arrangement. Likewise the spherical cavities, with insubstantial intersection, can also be layered in a worm-like manner or lined up adjacent to one another, e.g. in the form of closely adjacent spiral windings on the outer side of a hip joint shell, or in the arrangement of a projected fir branch, for example. A coarse structure of the surface of this kind, on which the spherical cavities are placed next to one another in a row as on a branch from which needles project laterally, has the advantage that ingrowing bone tissue can also build up blood vessels for its subsistence through the presence of worm-like sections along the axes of the worm-like structures due to the lesser rib height.

It is advantageous for the anchoring if the filigree network structure can be produced on curved or inclined surfaces in a rational manner. This is done in accordance with the characterizing portion of the independent claim 7 by the metal surface being covered over with an electrochemically active protective lacquer, with holes of diameter smaller than the interstice width or the diameter of the later spherical cavities respectively being left at a spacing of the later interstices; by the surface which is provided with holes in the protective lacquer being exposed to an electrolytic liquid for a limited time in order to produce sections of spherical cavities by electrochemical erosion or etching which are separated from one another by narrow ribs; by the remaining protective lacquer being removed; and by the coarsely structured surface being provided with a fine structure, for example by means of sand blasting. A further rational manufacturing method for an intermediary surface as a preliminary stage of the surface described in claim 1 results from the characterizing features of claim 9 in that the implant is first coated over by an adherent, electrochemically active protective lacquer which can be vaporized by a laser of a low energy density without the underlying metal being affected thereby. On the contrary, for sufficiently long wavelengths of laser light, the reflection by the metal can be exploited as well, in that the radiation is reflected back into the protective lacquer and in that less radiation is absorbed by the metal. In addition, a substantially lower powered and less expensive laser can be used than for the metal processing. Due to this energy threshold between the protective lacquer and the implant, the maintenance of a definite focal length in order to ablate the protective lacquer is much less critical. Thus holes can be produced in the protective lacquer without the focusing distance being precisely maintained, and by using a laser beam which is incident at an inclination to the surface. A field of holes is produced in the protective lacquer by the laser beam through relative motion between the surface and the laser head and through path dependent triggering of the laser beam, with the holes having the same center to center spacing as the later interstices but having a smaller diameter than the later spherical cavities.

In a further step, which is common to all manufacturing methods, this surface, which is provided with holes in the protective lacquer, is exposed to an electrically conductive liquid, an electrolyte, in order to produce cup-like depressions in the region of the holes with its help by electrochemical erosion and/or etching. Starting with the diameter of the holes in the protective lacquer and with the duration of the influence of the electrochemical erosion and/or etching, cup-like depressions arise which grow in depth and in diameter. It is a somewhat astonishing property of the method that, in the range of the predetermined dimensions for the interstice width and given the correspondingly smaller round holes in the protective lacquer, depressions practically always arise in the form of spherical cavities, which, depending on the duration of influence, can expand from a shallow spherical depression to a hemispherical depression, which in the most favorable case has an additional small cylindrical edge. A possible explanation for this effect are diffusion processes if only relatively small holes are present in the protective lacquer. The center to center spacing of the holes, the diameter of the holes and the acting time during erosion are chosen in such a manner that, when the erosion is discontinued, ribs with a desired wall thickness remain standing between two adjacent spherical cavities and a desired shell depth is achieved. This process has the advantage that the metal processing for the production of this intermediary form of the surface can be done simultaneously over large surface areas and within a few minutes. After removal of the electrochemically active protective lacquer, there is present an intermediary surface which receives a fine structure through sand blasting such that the topography as described above in claim 1 arises. With slight intersection of the spherical cavities, saddles arise at the narrowest locations, while peaks remain standing at the nodes where several ribs run together. Depending on the type of protective lacquer, the latter can be removed directly during the coarse blasting.

From the above description it follows that the method can be modified to the extent that a furrow is produced in the protective lacquer by the continuous evaporation off of protective lacquer along a predetermined line segment by means of a laser, which furrow produces a correspondingly broader groove in the metal during the subsequent electrochemical erosion. The cross-section of this groove corresponds substantially to a segment of a circle as long as the grooves have a width of 2 mm to 0.4 mm and the furrows are inscribed with a width which corresponds to a fraction of the width of the grooves. The advantage of such a method consists in the fact that the laser beam can be guided like a graving tool along arbitrarily curved or interrupted lines on a metal surface covered with protective lacquer in order to produce patterns which subsequently reproduce themselves as a coarse structure on the metal surface through the controlled electrochemical erosion or etching. The ribs left standing between the grooves form anchoring areas which can be effective transversely to possible shear stresses in the surface. One condition during the inscription by the laser is that the inscription speed and the intensity of the laser must also be matched to one another. A further condition for the protective lacquer and the intensity during electrochemical erosion or etching is that the intensity may be chosen only so strong that the protective lacquer, which is supported on one side only in the region of the furrow, does not crumble away while being undermined during the electrochemical erosion, in order to produce a reproducible coarse structure. After removal of the protective lacquer there remains a coarse structure of the surface with groove sections which can be closely layered and which can mutually penetrate one another. Here ribs can likewise be produced on a certain surface which are suitable for the anchoring of a metal implant, which, however, for the same smallest dimensions of the cavities, have a smaller sum of their edge lengths compared with the spherical cavities. In the extreme case, a grid of intersecting grooves of this kind can be produced in which the ribs have degenerated to protruding pins, the sum of whose edge lengths corresponds to a minimum.

Many products are suitable as an electrochemically effective protective lacquer which can be applied to metals, which can be drilled by a laser and which can be penetrated by an electrochemical liquid only in the region of the drilled holes. Decisive for the selection trials, however, was that, for reasons of economy with respect to the maintenance of cleanliness during the manufacture of the ingrowth surface, no further form-giving production operations on the implant should follow. The electrochemically effective protective lacquer should thus also be capable of effectively covering over sharp edged surface transitions such as those occurring at ribs or, for example, at latchings of hip joint shells. Corresponding products are mentioned as a protective lacquer in the exemplary embodiments. A protective lacquer is particularly suitable if, given a good adhesion, only a small layer thickness is required for insulation, since then a minimum layer thickness is easier to maintain even for sharp-edged transitions due to the thin layer thickness. A further advantage of thin protective lacquer coatings is that the gas bubbles arising during the electrochemical erosion and/or etching have less of a tendency to remain caught in the holes of the protective lacquer and thus to inhibit the erosion process.

Further advantageous improvements are achieved if the electrolytically eroding liquid is supplied within a bath transversely over the surface as an unconsumed jet and simultaneously washes away the arising gas bubbles. In salt solutions the implant is used as an electrode and should be contacted at a non-wetted region. A corresponding counter-electrode should be placed at a distance of less than 10 mm from the surface to be processed. The flushing is then done for example by a jet into the gap between the two electrodes. A different possibility are electrodes which have a hole pattern in the working gap through which fresh electrolyte is injected. The erosion can be metered very precisely via the duration of the applied voltage. By maintaining a certain temperature of the electrolyte, its conductivity and the current flow can be maintained more precisely. For certain metals, such as titanium for example, passivising layers can form, which can make a higher initial voltage necessary than for the actual erosion at voltages between 15 to 60 volts. For titanium a voltage of 40 volts in conjunction with a table salt solution has proven effective.

BRIEF DESCRIPTION OF THE DRAWINGS

FIG. 1b is a schematic enlarged section of FIG. 1a;

FIG. 3 is a schematic enlarged section of an intermediate surface in accordance with FIG. 1a;

DESCRIPTION OF THE PREFERRED EMBODIMENT

A surface 2 for a metal implant 1 is shown in the drawings. It has a coarse structure consisting of elevations 3 and depressions 4, with the surface 2 being traversed by a network 5 of protruding ribs 6 having nodes 7 and interstices 8 with an interstice width of 2 mm to 0.4 mm, while the depressions represent sections of spherical cavities 11. The nodes 7 of the ribs can protrude the most like mountain peaks, while ribs 6, which connect two nodes 7, form a lower lying saddle 10 if the spherical cavities penetrate one another slightly. Through covering with an electrochemically resistant protective lacquer into which holes are shot at a predetermined spacing without damaging the metal, with a laser, for example, a coarsely structured intermediate surface can be produced economically by means of electrochemical erosion, which receives a fine structure through sand blasting.

Figure 1A:
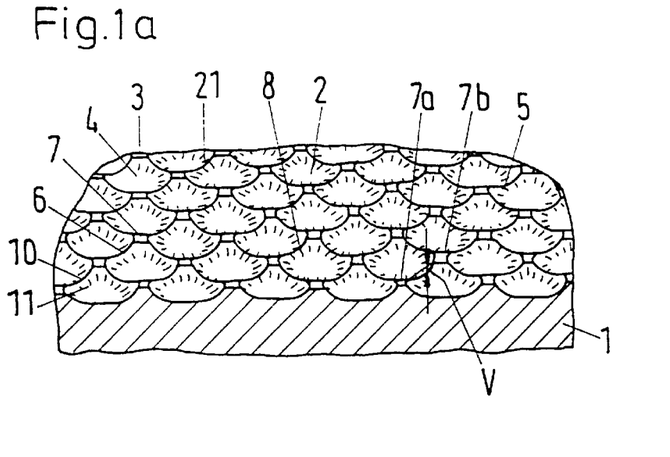
FIG. 1a is a schematic enlarged view of a section of a surface in accordance with the invention with mutually intersecting spherical cavities.
Figure 1B:
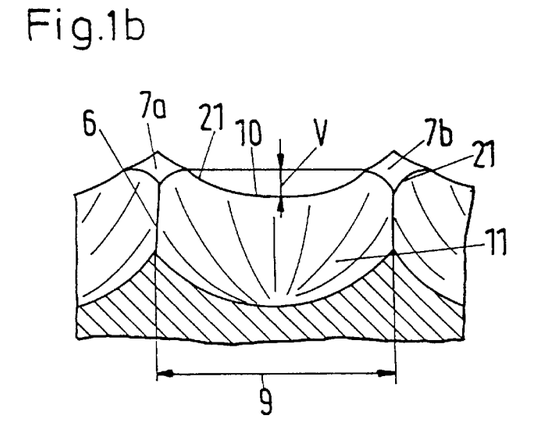
Figure 1C:
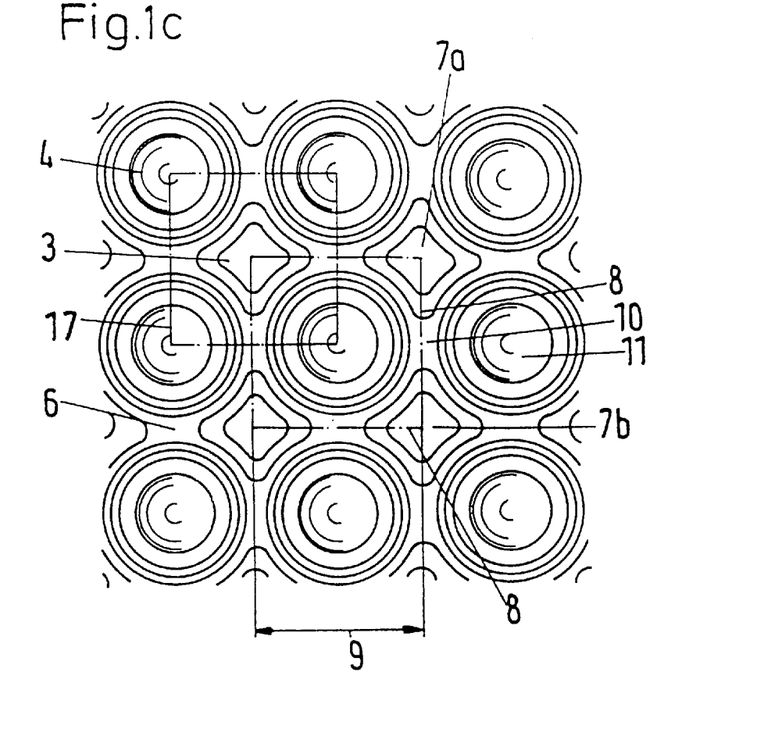
FIG. 1c is a schematic representation with contours of constant elevation for a quadratic grid in accordance with FIGS. 1a and 1b.
Figure 10:
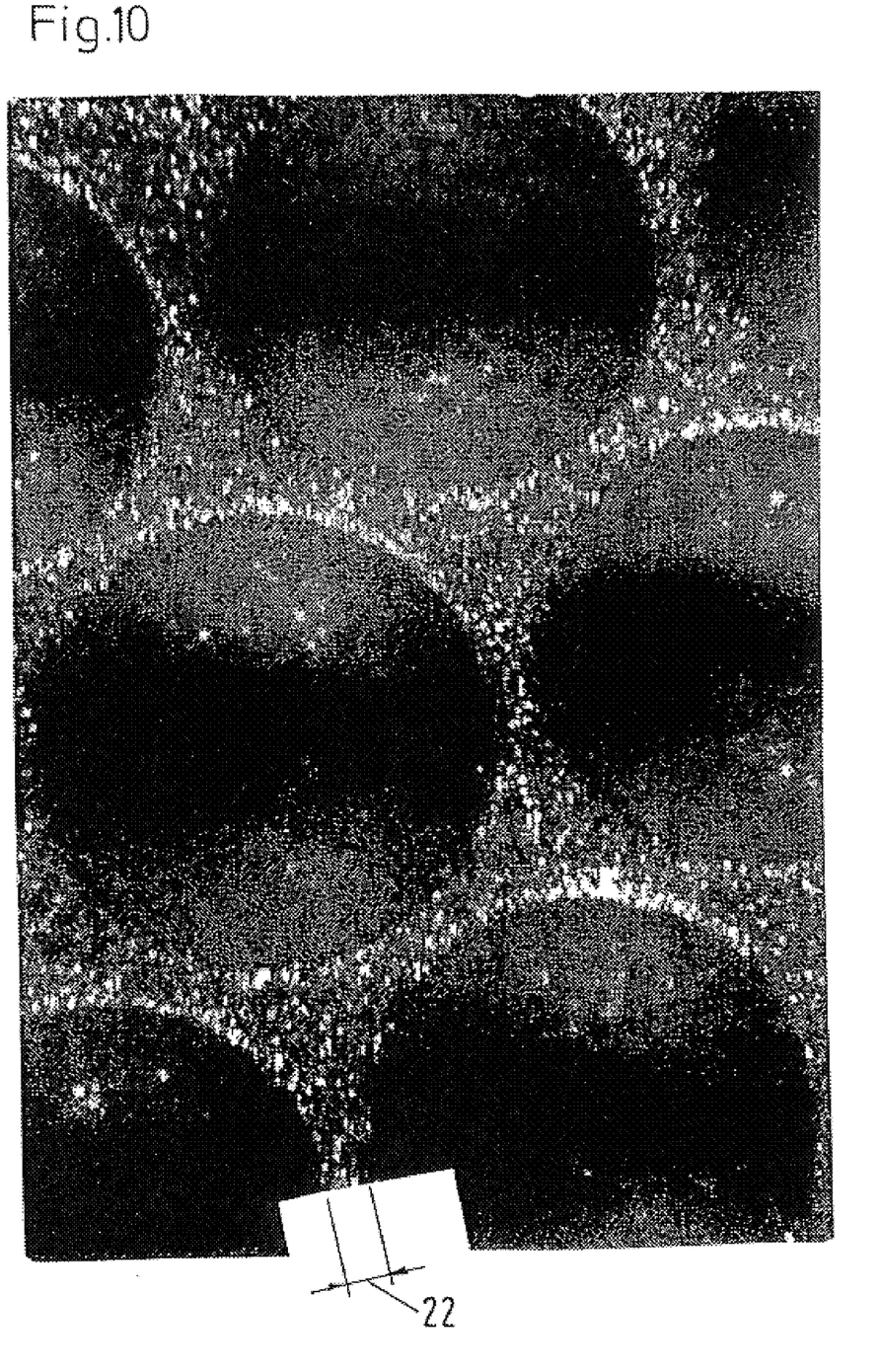
FIG. 10 shows an enlarged surface on an implant of metal with spherical cavities which do not mutually intersect.

A finished processed surface 2 of a bone implant 1, which has elevations 3 and depressions 4, is shown in FIGS. 1a, b, c. The elevations 3 consist of a network 5 of protruding ribs 6 which have nodes 7 and interstices or meshes 8 with an interstice or mesh width 9 of 2 mm to 0.4 mm and edges 21. The midpoints of the interstices 8 are arranged in a square grid in this exemplary embodiment, whereas they are arranged in a grid consisting of equilateral triangles in the example of FIGS. 1d at spacings 17 in order that the ribs 6 have the same constitution and length independently of their direction. The depressions 4 are formed by sections of spherical cavities 11 whose axes pass through the midpoint of the interstices 8. At their nodes 7, the ribs 6 protrude the furthest in the manner of peaks 7a, 7b, while, as the connection of two such nodes 7a, 7b, they form a lower lying saddle 10 which is located at an amount V lower than the peaks 7a, 7b. Such saddles 10 arise when the spherical cavities overlap somewhat. This need not necessarily be the case, however, since a filigree network 5 of ribs remains standing even if the spherical cavities 11 just fail to overlap. FIG. 10 shows the enlargement of a photographed surface with spacings 17 in a grid of equilateral triangles analogous to FIG. 1d, however without overlapping of the spherical cavities. The interstice width 9 amounts to 1.0 mm here and the minimum width of the ribs amounts to somewhat less than 0.1 mm. The spherical cavities 11 have a diameter of somewhat more than 0.9 mm and have a depth 12 of 0.4 mm. Although the implant in FIG. 4 is of relatively soft titanium, a wall thickness 22 of ≈0.1 mm at the narrowest cross-section of the ribs is sufficient for an anchoring, since the cross-section increases away from the minimum width in the depth direction and along the rib. This effect is further enhanced if the spacings 17 are chosen in a square grid as in the example of FIGS. 1a, b, c.

Figure 1D:
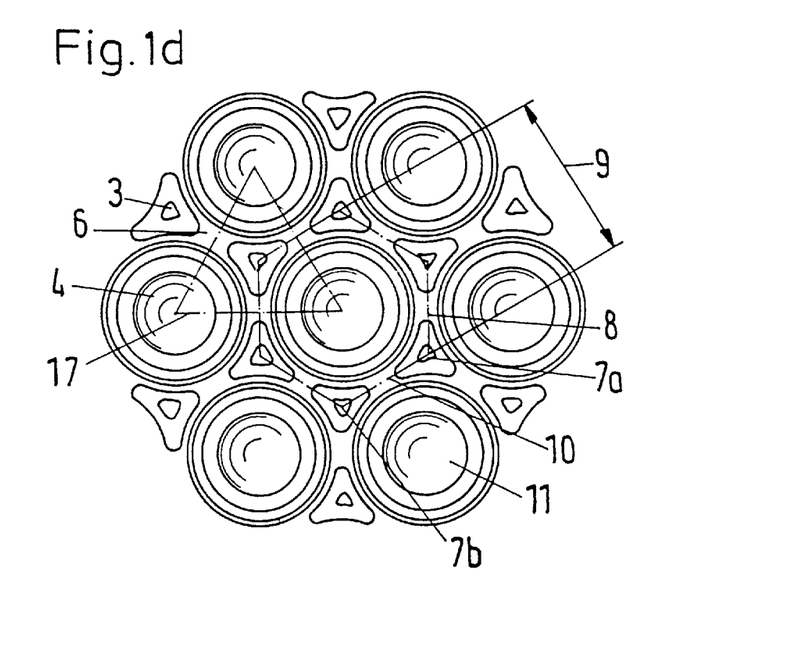
FIG. 1d is a schematic representation with contours of constant elevation in accordance with FIG. 1c, but for a grid which is composed of equilateral triangles.
Figure 2:
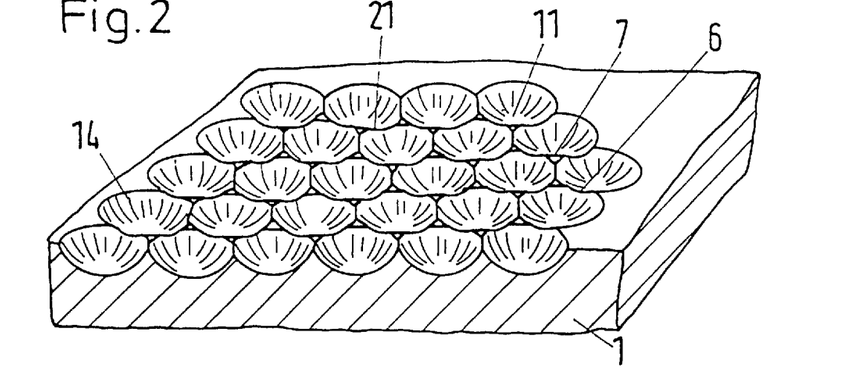
FIG. 2 is a schematic enlarged view of an intermediate surface in which the spherical cavities are arranged in a grid analogous to FIG. 1d.
Figure 3:
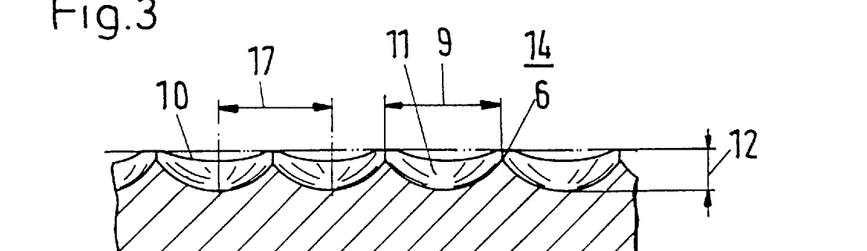
Figure 4A:
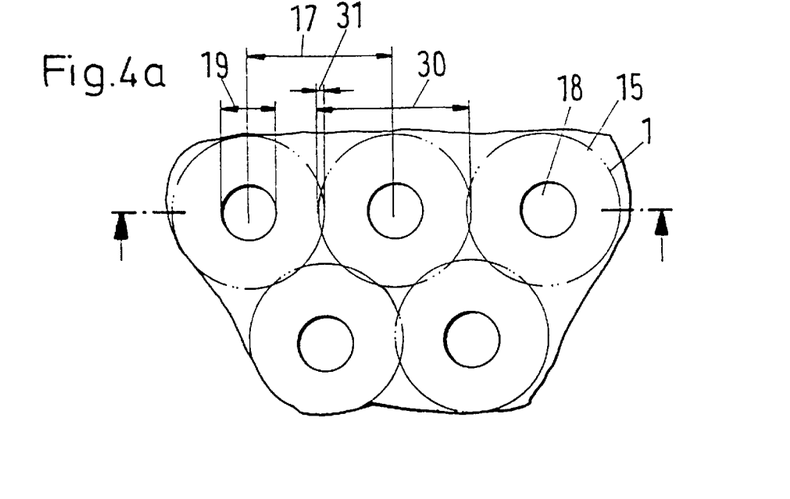
FIG. 4a is a schematic enlarged plan view of a surface which is coated with protective lacquer, with the holes for the electrochemical erosion having already been produced in the protective lacquer.
Figure 4B:
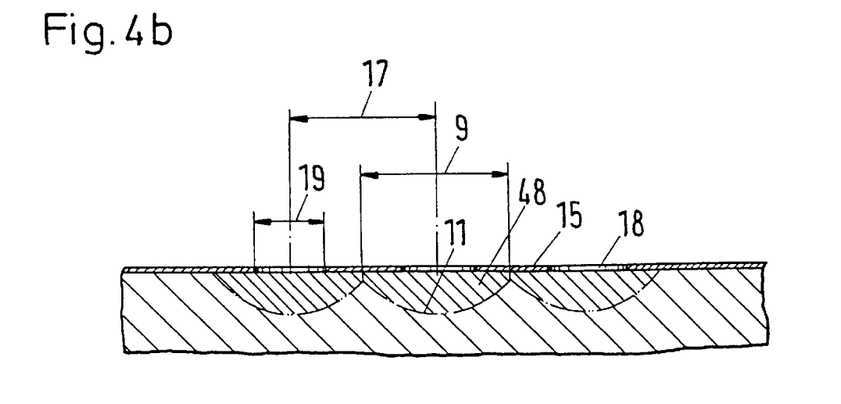
FIG. 4b is a schematic section through a surface in accordance with FIG. 4a in which however, the diameter of the holes in the protective lacquer has been chosen larger in order to produce shallower spherical cavities.
Figure 4C:
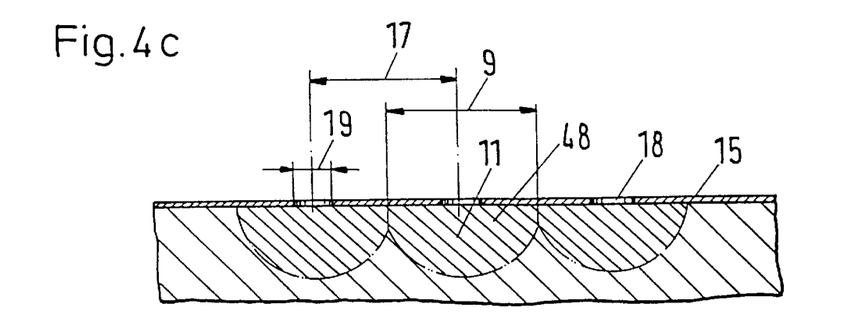
FIG. 4c is a schematic section through a surface in accordance with FIG. 4a in which, however, the diameter of the holes in the protective lacquer has been chosen smaller in order to produce deeper spherical cavities.

FIGS. 2 and 3 show an intermediary surface 14 as a preliminary manufacturing stage of a surface 2 in accordance with a spacing 17 of the spherical cavities 11 in a triangular grid of FIG. 1d whose production is described in the following. As an intermediate surface, spherical cavities 11 with a diameter 30 which is greater than the distance between their midpoints are produced in order to allow ribs 6 with a saddle 10 to remain standing within the framework of the attainable manufacturing precision. For this purpose the originally smooth initial surface of FIGS. 4a, 4b, 4c is covered over with an electrochemically effective protective lacquer 15 in such a manner that apertures in the form of holes 18 with a diameter 19 that is substantially smaller than the diameter 30 of the spherical cavities 11 are produced in a grid with spacings 17. Subsequently the surface which is provided with holes 18 in the protective lacquer is exposed to an electrolyte, with an electrochemical erosion or etching taking place in the region of the holes. The duration of the action of the electrochemical erosion must be adapted according to the undersize of the holes 18 with diameter 19 relative to the desired diameter 30 of the spherical cavities 11. For a lesser undersize (FIG. 4b), short acting times and shallower spherical cavities 11 result. For a large undersize (FIG. 4b), longer acting times and deeper spherical cavities 11 result. As a limiting value, 60% of the diameter of a hemisphere can be assumed to be a manageable depth 12 of the spherical cavities. In such a case, the first 10% of the depth extends approximately cylindrically up to the hemispherical cup. After the electrolytic machining the intermediate surface 14 is present except for the adhering protective lacquer 15. Depending on the kind of protective lacquer, the latter can be removed by a solvent, chemically, by the action of heat and/or mechanically in order to arrive at an intermediate surface 14, which receives a fine structure through sand blasting. If the protective lacquer 15 can be removed mechanically through sand blasting, its removal and the production of the final structure can be performed in a single operation.

Figure 1E:
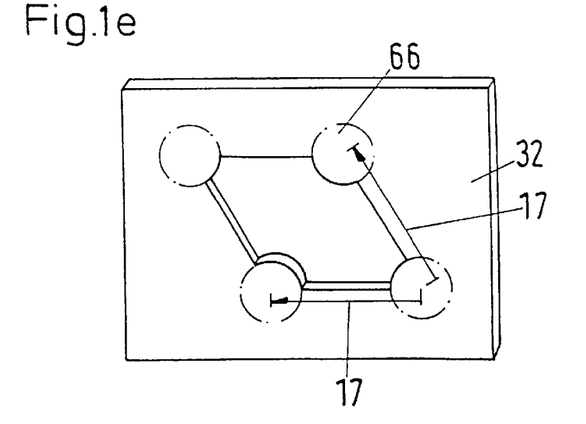
FIG. 1e is a schematic representation of a mask which can be displaced stepwise in order to exclude the holes later required for the etching from a hardening triggered by irradiation.

The cutting out of the holes or, respectively, the hardening of the protective lacquer outside the holes 18 can also be performed by photochemical effects, for example with the protective lacquer being hardened by irradiation outside the holes 18 through a mask and washed out in the region of the non "exposed" holes in order thus to achieve the prerequisites for the electrochemical erosion. A mask 32 suitable for FIG. 1d is shown in FIG. 1e, with the displacement paths between the irradiations being indicated in a grid with spacings 17. Polymers which can be hardened by a photoeffect can also be considered as a protective lacquer.

A useful possibility consists in applying the protective lacquer 15 to the whole surface and allowing it to harden, then subsequently vaporizing off the protective lacquer in the region of the holes 18 with a laser. Here it is advantageous if the metal in the region of the holes is neither liquefied nor vaporized.

EXAMPLES

When using protective lacquer products of the group poly-para-xylylene like PARYLENE or poly-chloro-para-xylylene like PARYLENE "C"; of the Union Carbide Corporation, which is marketed by Nova Tran Ltd., Precision Surface Polymers, Northampton, UK, the application is performed in a vacuum by vaporization of the poly-para-xylylene, which condenses on the surfaces and polymerizes. The parts are placed in a vacuum oven on hanger devices such as in FIG. 7a, for example, where the PARYLENE is vaporized at 600° C. The deposited layer grows at about 2 $\mu$m per hour, with regions even difficult of access being well covered. A thickness of 3 $\mu$m<S<10 $\mu$m is sufficient for an insulating layer thickness for the electrochemical erosion, with layer thicknesses up to 100 $\mu$m being possible. A thickness S of 7 $\mu$m has proved to be a safe layer thickness at which even sharp edged transitions are still adequately covered. For thicknesses less than 5 $\mu$m the protective layer could be peeled off at certain places by a flushing jet 33 (FIG. 7b) during the electrochemical etching. When the application is done in a vacuum, thicknesses of over 10 $\mu$m are not very economical.

Figure 5:
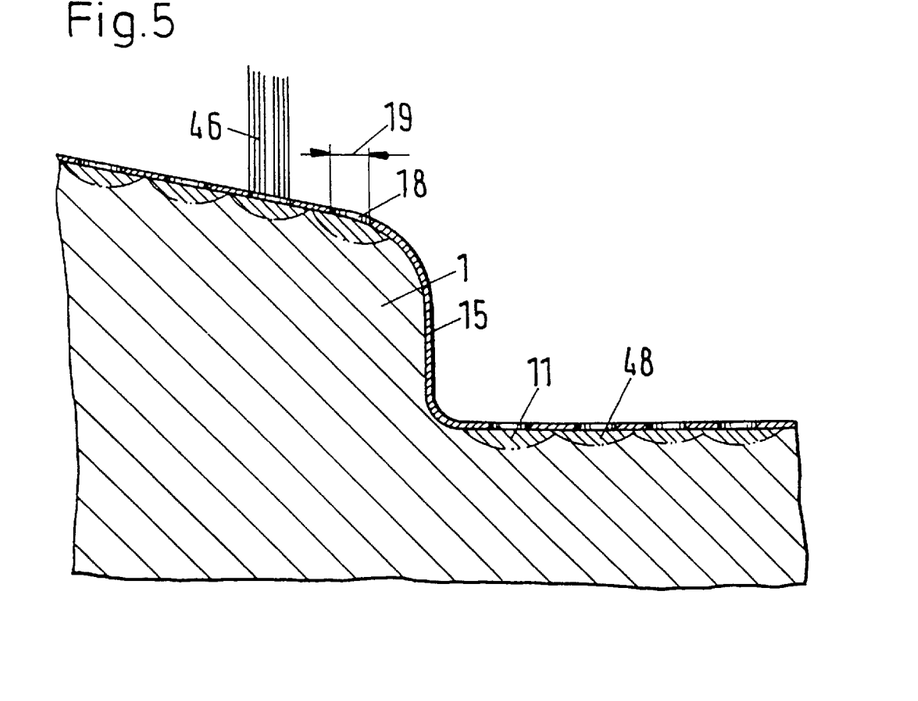
FIG. 5 is a schematic enlarged section through a stepped surface which is coated with protective lacquer, with the holes for the electrochemical erosion having already been produced in the protective lacquer.
Figure 6:
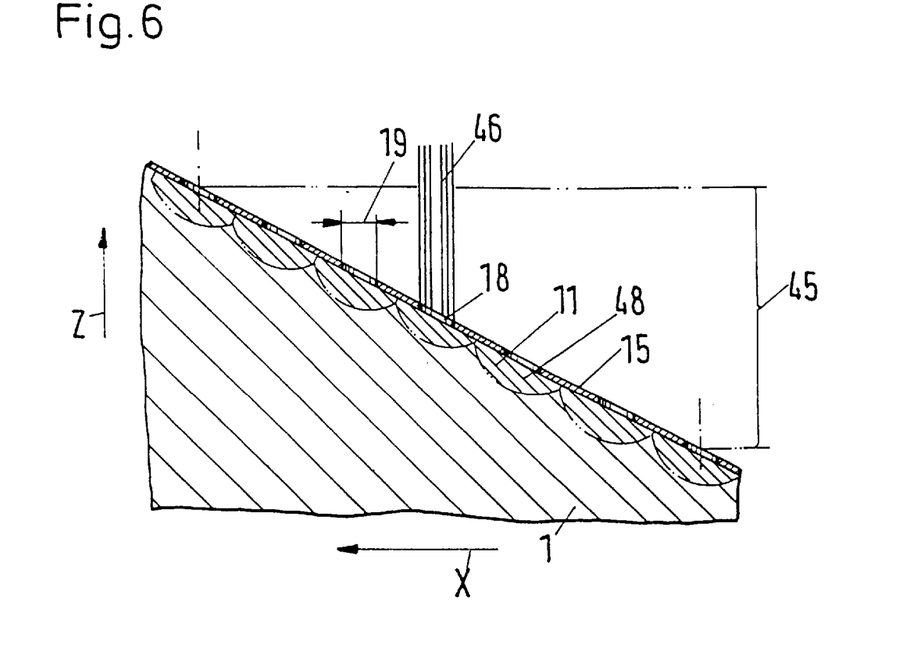
FIG. 6 is a schematic enlarged section through a surface which is coated with protective lacquer and stands at an inclination to a laser beam, with the holes for the electrochemical erosion having already been produced in the protective lacquer.
Figure 8A:
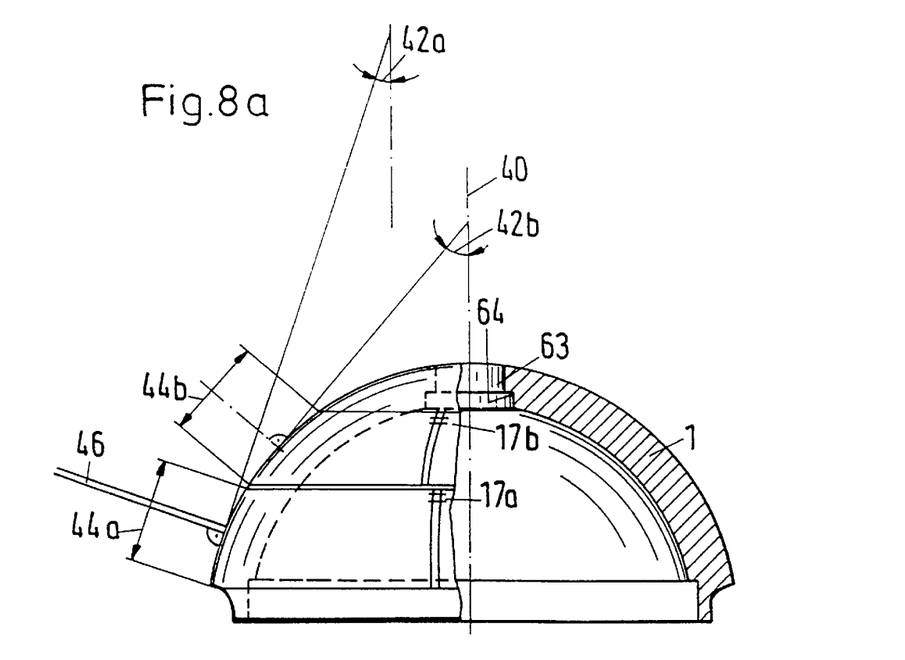
FIG. 8a is a schematic enlarged section of a hip joint shell at which a subdivision of the spacings for the holes in the protective lacquer is shown for two circumferential bands.
Figure 8B:
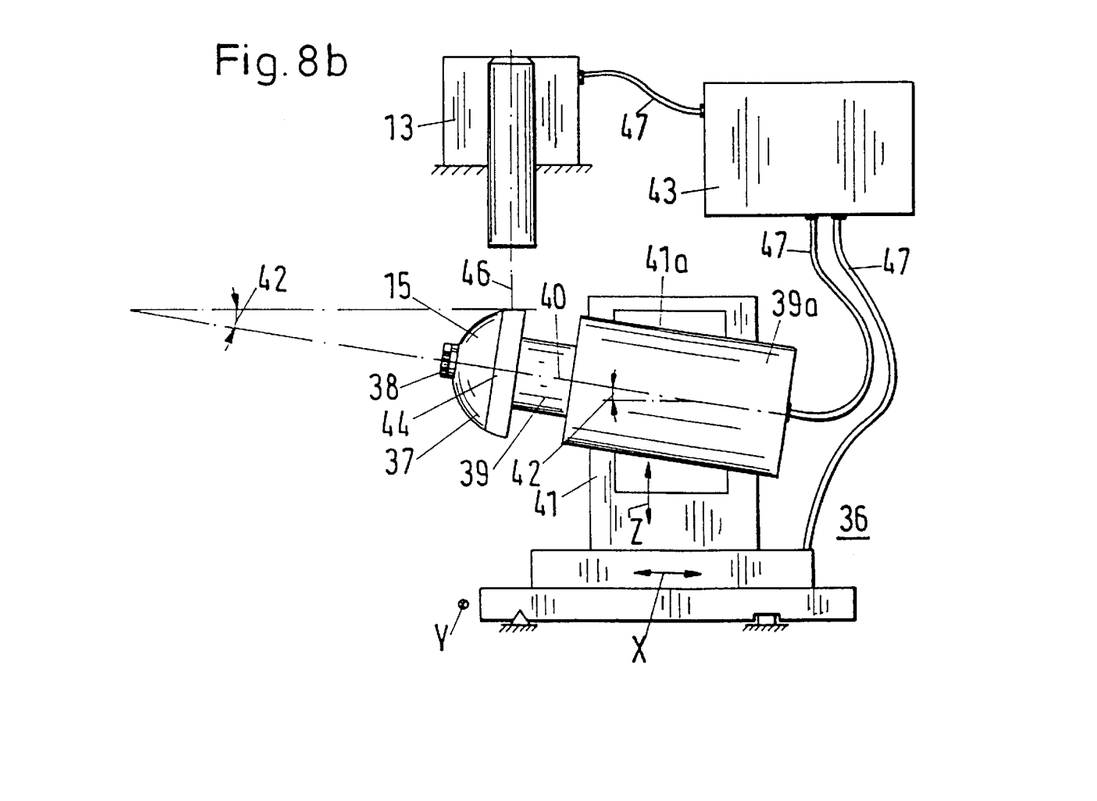
FIG. 8b shows a schematic arrangement for producing the holes in the protective lacquer of a hip joint shell in accordance with FIG. 8a using a laser.

In an arrangement in accordance with FIG. 8b the PARYLENE appears as a thin transparent protective film on the implant, which, for the production of the holes 18, is mounted in a numerically controlled mounting apparatus 36 in order to drill the holes 18 in the protective lacquer 15 with a laser 13. In FIG. 8b a hip joint shell 37 is fastened by means of a fastener screw 38 to a rotatable spindle 39, with the spindle axis 40 coinciding with the polar axis of the hip joint shell. The mounting apparatus 36 consists of a stand 41 which stands on a compound table that is movable in the x and y directions and accommodates a vertical carriage for the vertical direction z. A laser 13 is mounted perpendicular to the compound table and is coordinated with the numerically controlled mounting apparatus 36 via a control system 43 in such a manner that it shoots a hole pattern into the protective lacquer in accordance with a predetermined grid. For this purpose, the control system 43 is connected by means of connection lines 47 to the laser 13, to the mounting apparatus 36 and to the spindle drive 39a of the spindle 39, which is fastened to the vertical carriage 41a at a pivotal angle 42. In FIG. 8a the surface to be processed consists of two bands 44a and 44b which extend parallel to the equator. Since, in accordance with FIG. 6, the readjustment of the focus for a hole 18 is not necessary for a depth change of <8 mm, the holes 18 can already be produced, as shown in FIGS. 5 and 6, in surfaces which are stepped or oriented at an inclination to the laser beam 46 by displacement with the compound slide in an x-y plane within the permissible depth change 45. Since the pivotal angle 42, 42a, 42b is formed with a tangent at one band 44, 44a, 44b which extends parallel to the compound table, a trapezoidal hole pattern of a grid 17 is mapped in the coordinates of the compound table with only insubstantial distortions 17a, 17b and without movement along the z axis. The spindle 39 is rotated further in each case by a certain division so that trapezoidal, slightly distorted hole patterns are arrayed side by side on the periphery of the band 44. It is equally possible to provide the rotary spindle 39 with a numerically controlled fine adjustment and to produce a hole pattern using a program for a spindle drive 39a and for displacements in the x axis.

Figure 8C:
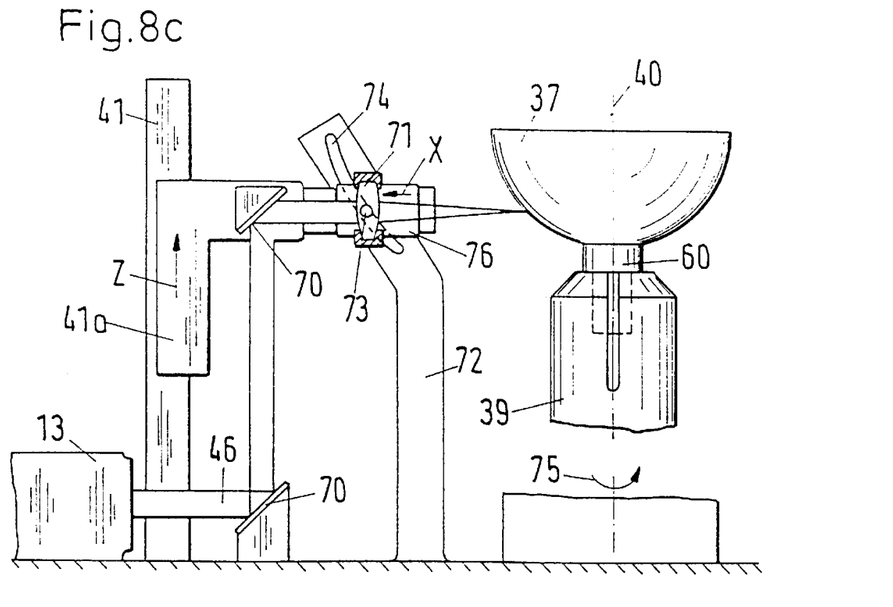
FIG. 8c shows a further schematic arrangement with a laser for producing the holes on a hip joint shell coated with protective lacquer.

A further possibility for the partial compensation of the depth adjustment in contrast to a horizontal laser beam 46 is shown in FIG. 8c. The laser beam 46 is displaceable in the vertical direction via two 45 degree mirrors 70, of which the one is displaceably mounted on a vertical carriage 41a. The parallel emerging laser beam is focused by means of a lens 71, which is in turn fixed on a horizontal carriage 76 and is horizontally displaceable with respect to the vertical carriage 41a. The laser beam is focused onto the surface of a hip joint shell 37, which itself is fixed by a clamping bolt 60 in a numerically controlled rotary spindle 39 in such a manner that the polar axis and the spindle axis 40 coincide. Through a controlled rotational movement 75 all points which lie at the same latitude can be approached, while for the displacement of the focus along a meridian, the vertical carriage 41a is vertically displaced in the Z direction in a numerically controlled manner and a correction of the lens spacing in the horizontal plane is simultaneously carried out. This correction necessarily occurs here along with the height adjustment of the vertical carriage 41a through the horizontal carriage 76 being guided by a pin 73 in a guidance groove 74 which is displaced approximately parallel to the meridian of the hip joint shell 37. The guidance groove 74 is machined into a stand 72 of fixed spatial location. It need not extend exactly parallel to the surface of the workpiece, since the distance of the focal point may fluctuate in the range of up to 8 mm in order to shoot sufficiently precise holes into the protective lacquer.

In FIGS. 5 and 6, the holes 18 with diameter 19 are indicated along with the spherical cavities 11 which are not to be produced until later by means of electrochemical erosion—the latter being indicated by closer hatching 48.

Further examples for the application of protective lacquer:

Other kinds of protective lacquer 15 can be applied by different methods to the implant 1 a phenol resin soluble in methanol, such as the product CHEMLOCK 104 of the Henkel Corporation, for instance, can be applied by immersion lacquering, epoxy resins containing phenol such as the product GOLDLACQUER of the Holden Corporation or CASCOPHEN of the Barden Corporation can be applied by spray lacquering, a further possibility consists in electrostatic powder coating, in order to provide conditions similar to those represented in the FIGS. 5, 6 8a, 8b for the drilling of holes 18 in the protective lacquer 15 using laser beams without damaging the metal lying thereunder.

Figure 9:
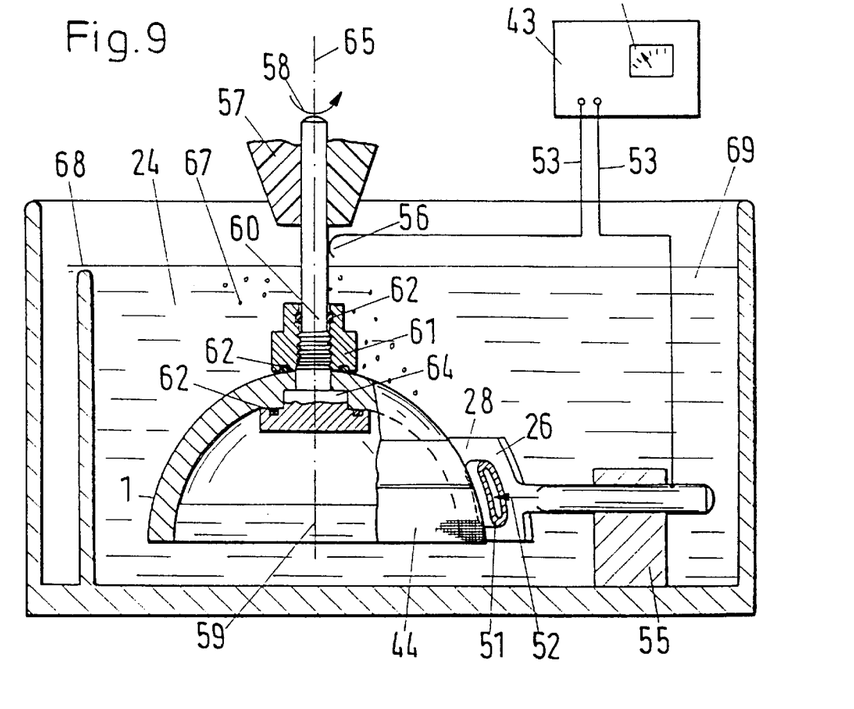
FIG. 9 schematically shows, the electrochemical processing at an outer shell in accordance with FIGS. 8a, b, c.

An outer shell 1 illustrated in FIG. 8a for an artificial hip joint can be secured at the pole side to a stepped mounting bore 63 for the application of protective lacquer, with a shoulder 64 shown in FIG. 9 receiving no protective lacquer in order for a metallic contact to be possible for a current transfer. This mounting bore 63 with a shoulder 64 serves simultaneously as a fastening surface and counter-surface for the fastener screw 38 in FIG. 8b during the laser drilling of protective lacquer, while in FIG. 9 a clamping bolt 60 with a counter-nut 61 is arranged in such a manner that the exposed locations provided for the centering and the current transfer are sealed off against contact with the electrolyte 24 via soft seals 62.

In the arrangement of FIG. 9 an outer shell 1 with a hole pattern 44 is shown fastened to the tensioner bolt 60. The tensioner bolt 60 is clamped in a slowly rotating insulating clamping claw 57 in such a manner that the bearing shell 1 rotates about its polar axis, with the rotation 58 amounting to a few rotations per minute. For example, 5 rotations per minute are typical. The bearing shell 1 rotates in an electrolyte bath 69 which has an overflow 68. A control system 43 connects the bearing shell 1 to an electrical potential via an input lead 53, a sliding contact 56 and via the clamping bolt 60. A counter-electrode 26 is connected via an input lead 53 to a further potential, whose difference can be read off for example via a display 54 at the control system 43. The counter-electrode 26 is fastened to a stand 55 and led around a sector of the bearing shell 1 in the form of a flat electrode in order that a channel with a width of less than 10 mm arises in the region of the hole pattern 44 into which fresh electrolyte 52, for example a table salt solution, is injected via a flattened flushing tube 51. When a suitable voltage is applied between the electrodes, an electrochemical metal erosion takes place in the region of the holes placed in the protective lacquer. The metal ions enter into solution and form salts, while gas bubbles 67 simultaneously arise which could inhibit the process if they are not flushed out of the work region as a result of the dynamics of their origin and by means of the flushing jet. The size of the arising spherical cavities 11 can be very precisely maintained through a limitation of the current and a monitoring of the switch-on time.

Figures 7A, 7B:
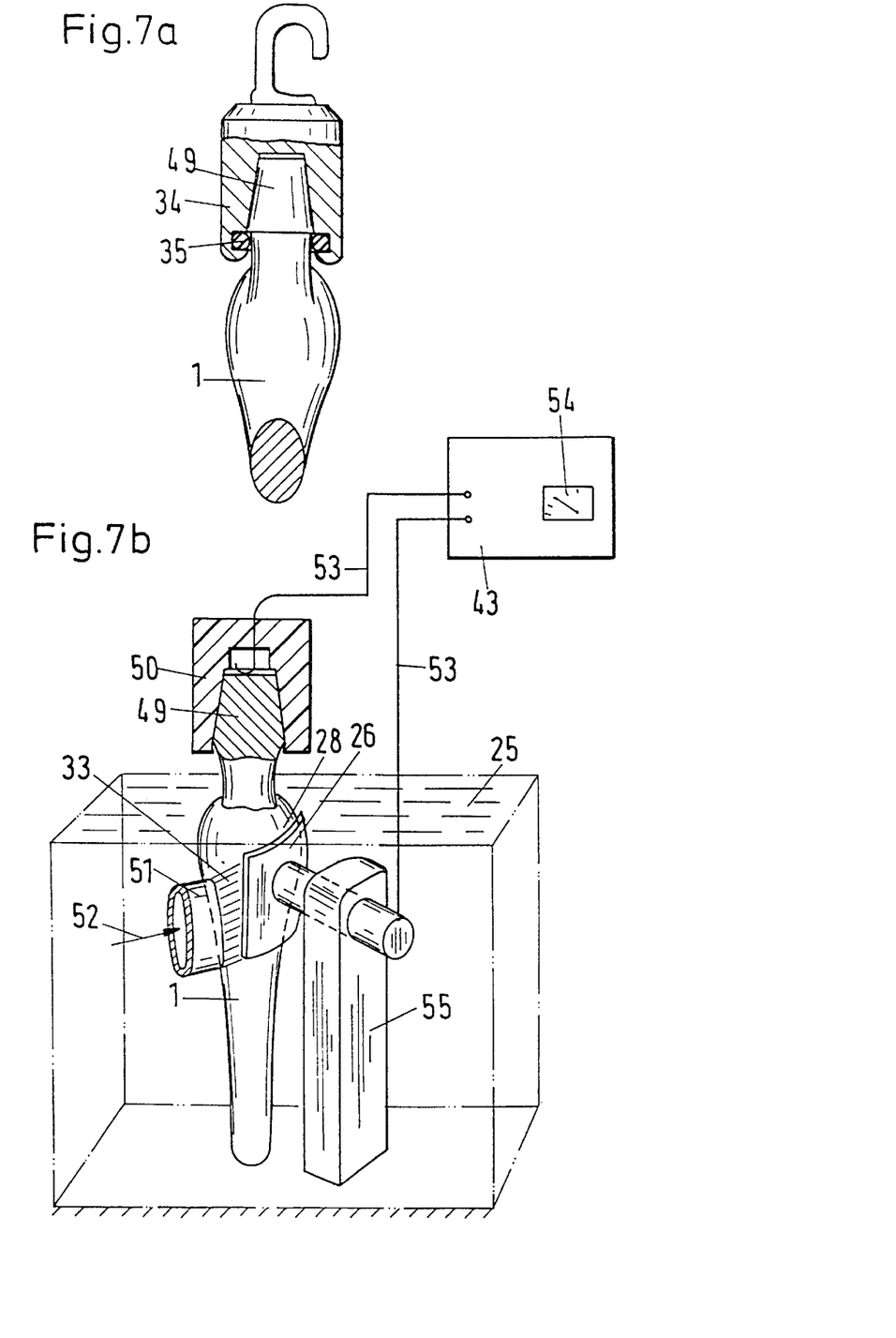
FIG. 7a schematically shows, the fixing of a femur shaft for a coating with protective lacquer.
FIG. 7b schematically shows, the fixing of a femur shaft during electrochemical erosion.

A further example of a prosthesis shaft 1 is shown in FIGS. 7a, 7b. The prosthesis shaft can be secured with its cone 49 in a suspension apparatus in FIG. 7a in order to apply the protective lacquer. A sealing ring keeps the cone 34 free of protective lacquer in order that it can be used for mounting in an electrode holder 50 in accordance with FIG. 7b after the holes 18 have been drilled in the protective lacquer 15. The current transfer takes place via a resilient contact on the end face of the cone 34. The prosthesis shaft 1 is mounted at a fixed position in the electrode holder 50 and stands in an electrode bath, a table salt solution 25, together with a counter-electrode 26, which follows the contour of the shaft as a flat electrode and forms a channel 28 into which cleansed electrolyte is injected in a flushing jet 33 via a flushing tube 51. Here the throughflow quantity amounts to 10 l/min. or more if the channel 28 extends over an area of 15 $cm^2$ at the workpiece. This corresponds roughly to a speed of 400 mm/s in the channel 28. A typical arrangement for an electrode would be a flat electrode which has a distance of 2 mm from the drilling pattern and whose edges are shortened by about 4 mm in each direction with respect to the drilling pattern, if the work is to be done with a saturated table salt solution.

The current density should as a rule be held between 2 to 10 $A/cm^2$ in order that the arising gas bubbles assist the erosion process by ejecting eroded material out of the depressions 11.

The advantages of using a table salt solution as the electrolyte consist in the fact that a relatively simple recycling of the electrolyte is possible through filtration, in that the electrolyte is simple to manufacture, and in that the electrolyte poses no risks for the operating personnel or the future bearer of the implant.

The electrodes 26 can be manufactured of carbon or metal, with brass being preferable since it is easy to machine and does not corrode during electrochemical erosion in a table salt solution.

In FIG. 7b the counter-electrode 26 is likewise mounted in a fixed location on a stand 55. The workpiece 1 and the counter-electrode 26 can be connected to a voltage source in a control system 43 via input leads 53. The voltage and current values are adjustable and can be read off from displays 54.

Figure 7C:
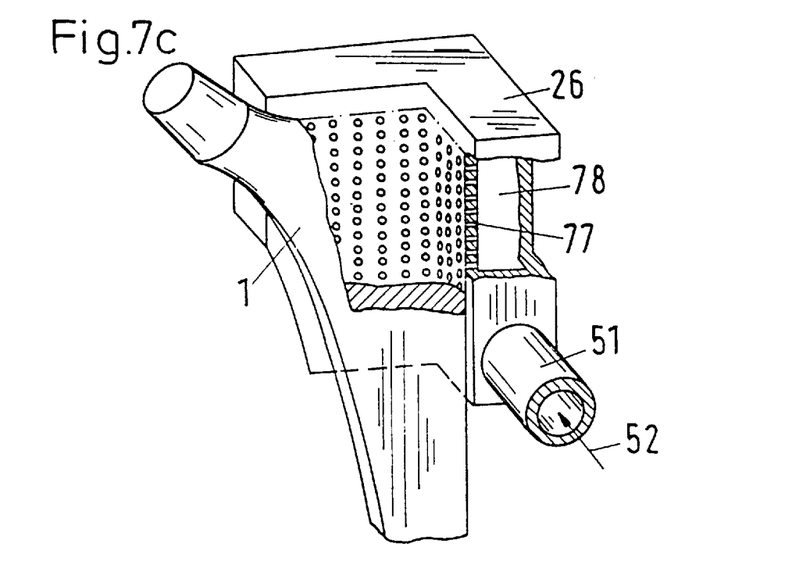
FIG. 7c schematically shows, an electrode with a hole pattern for introducing the electrolyte into the erosion gap.

A counter-electrode 26 is shown in FIG. 7c which has a narrow gap to the workpiece 1 in the envisaged erosion region and injects fresh electrolyte into the working gap via a plurality of bores 77. The bores 77 end in a cavity 78 which is supplied with fresh electrolyte 52 via a flushing tube 51.

Figure 11:
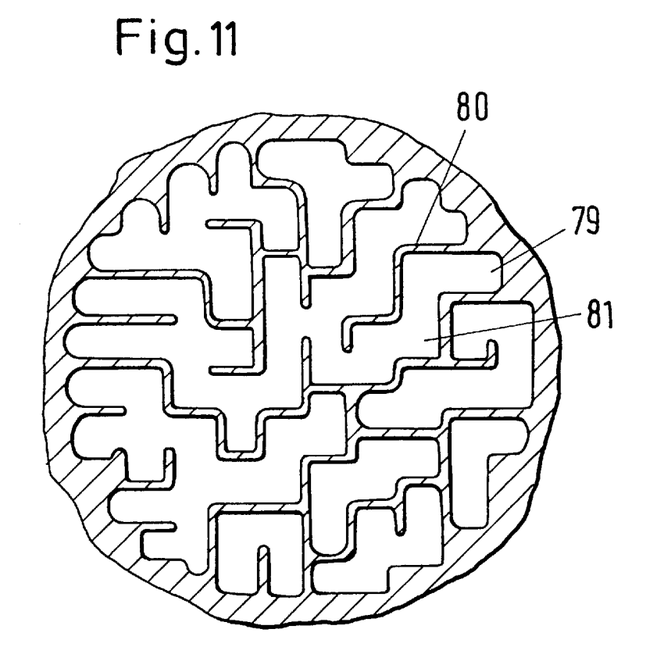
FIG. 11 schematically shows, an enlarged section below the envelope curve of an implant in which intertwining grooves with thin intermediate ribs are produced in an orthogonal arrangement.
Figure 12:
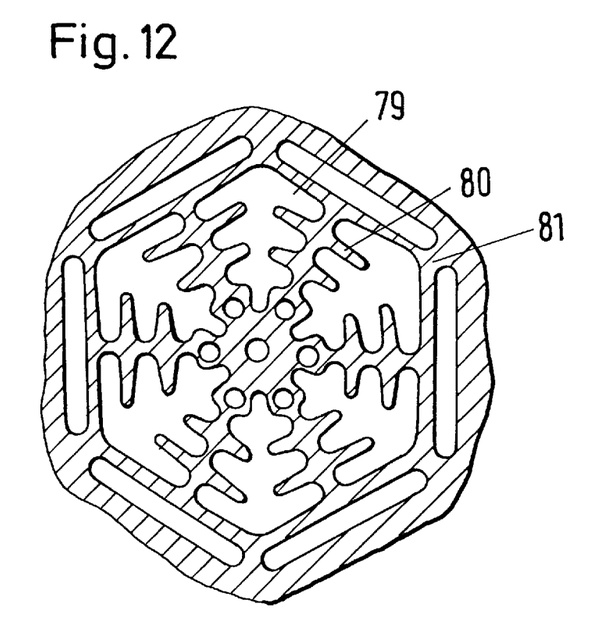
FIG. 12 schematically shows, an enlarged section below the envelope curve of an implant in which grooves which are separated by thin intermediate ribs form Christmas-tree-like structures in the form of a hexagonal surface element.

Two further examples for the shaping of implant surfaces are shown in FIGS. 11 and 12. Furrow sections inscribed by means of the laser into the protective lacquer cause groove sections 79 to arise during the subsequent electrochemical erosion which more or less interpenetrate and which are separated from one another by ribs 80 which are left standing. The blood supply of the ingrowing tissue is improved through the larger connected surfaces here. Larger blood vessels can arise along the groove sections 79. FIG. 11 shows a confused orthogonal network as a subsurface 81 which can cover larger areas through repetition. FIG. 12 shows a subsurface 81 built up as a hexagon with Christmas-tree-like structures which likewise facilitate the growing in. Subsurfaces of this kind have the advantage that they can also be lined up next to one another or adjacently even on curved surfaces during the inscription with the laser without too great a distortion arising.

The precise inscription of groove sections can be most simply managed with a multiple axis numerical control which prescribes the relative movement between the implant and the laser during the inscription.

The surfaces described here and the methods for their manufacture can also be applied quite generally to other fields in which a metallic substrate is provided with a structure consisting of elevations and depressions in order to produce a better connection to another material. Thus the bearing shells of sliding bearings can be provided with a structure of this kind before the actual bearing material is applied, irrespective of whether the bearing material is pressed on, such as TEFLON, for example, or whether the bearing material is sprayed on metallically.

It is likewise possible to provide the metallic surface of pressing tools, injection tools or rollers with this coarse structure which can be transferred as a negative to other parts, for example parts made of plastic, by means of form reversal.

The individual steps of the procedure itself can be improved by additional measures. Thus the effect of a salt solution can be improved during electrochemical erosion in that it is held at a constant and slightly elevated temperature which lies between 50° C. and the boiling point. Furthermore, the erosion can be improved through rapid movement of the workpiece in the erosion fluid in that for example the workpiece is mounted in an ultrasonic head like a sonotrode during the erosion. 25 kHz is a typical frequency for an ultrasonic oscillator which moves a workpiece of the size of an artificial hip joint. It is however also sufficient to shake the workpiece with a frequency of 50–100 Hz in that an oscillatory exciter is allowed to act on the suspension of the workpiece.

What is claimed is:

1. A method for manufacturing a coarsely structured metal surface of a metal implant comprising in a first step, coating the metal surface with an adherent, electrochemically active protective lacquer or coating which can be eroded by a laser of selected wavelength at such a low energy density that there is a significant energy threshold with respect to the energy density required for metal erosion, to preclude metal erosion, in a further step, shooting holes into the protective lacquer using the laser of selected wavelength in accordance with spacings of the envisaged spherical cavities, diameters of the holes being smaller than diameters of spherically shaped cavities to be formed subsequently, in an additional, step, exposing the surface which is provided with holes in the protective lacquer to an electrically conducting liquid to produce the spherically shaped cavities over a limited time by electrochemical erosion and/or etching so that they grow simultaneously in depth and parallel to the surface in the region of the holes, and removing the remaining protective lacquer in a further step.

2. A method in accordance with claim 1 characterized in that in the first step, poly-para-xylylene is applied as a monomer to the implant as a protective lacquer by evaporation in a vacuum for polymerizing it to a protective film with a thickness of 3 $\mu$m<S<100 $\mu$m, preferably with a thickness of 5 $\mu$m<S<10 $\mu$m, a model of laser is used which produces a more than 50 times lower energy density at a focal point of the holes than for the melting and welding of metal, for a poly-para-xylylene layer with a thickness S=7 $\mu$m, a 25 watt $CO_2$ laser which produces an energy density of 2 J/mm$^2$ at a wavelength of 10.6 $\mu$m, and salt solutions, solutions of potassium bromide, of sodium nitrate, of sodium chlorate or dilute acids are used as the electrically conducting liquid in order to erode or to etch electrochemically with electrical assistance.

3. A method in accordance with claim 2 characterized in that cleansing operations are provided as preparatory or as intermediary steps.

4. A method according to claim 2 wherein the poly-para-xylylene is a poly-chloro-para-xylylene.

5. A method in accordance with claim 1 characterized in that a table salt solution is used as the electrically conducting liquid for an implant of titanium or of a titanium alloy; and in that an electrical voltage is applied temporarily in the salt solution between the implant and an electrode in order to achieve a predetermined size of the round cavities arising at the holes during the time of action.

6. A method in accordance with claim 1 characterized in that a minimum voltage <100 volts is applied to the implant for electrochemical erosion in order to remove passivating layers, whereas the actual erosion takes place at voltages between 15 and 60 volts, for titanium preferably at a voltage of 40 volts.

7. A method in accordance with claim 1 characterized in that a phenol resin soluble in methanol is used as a protective lacquer.

8. A method in accordance with claim 1 characterized in that an epoxy resin containing phenol is used as a protective lacquer.

9. A method in accordance with claim 1 characterized in that the protective lacquer is applied by electrostatic powder coating.

10. A method in accordance with claim 1 characterized in that after the etching or electrochemical erosion the residual protective lacquer coating is embrittled in a fissured manner at temperatures less than 400° C., by one of hot air or infrared heat to subsequently remove it mechanically, by means of one of sand blasting or a caustic etch.

11. A method in accordance with claim 1 characterized in that a laser with a wavelength greater than 2 $\mu$m is used in order to partially achieve a reflection at the metal surface.

12. A method in accordance with claim 1 characterized in that, for the production of different depths with a given diameter of the spherical cavities at intermediate surfaces by one of keeping the diameter of the holes in the protective lacquer small and lengthening the etching time to produce deep hemispherical cavities and keeping the diameter of the holes in the protective lacquer large and shortening the etching time to obtain shallow sections of spherical cavities.

13. A method in accordance with claim 1 characterized in that during the electrochemical erosion an areal electrode is arranged at a distance of between 1 mm to 10 mm from the implant and covers at least a part of the implant with its surface to form a channel, with the current density across the channel being kept less than 20 A/cm$^2$.

14. A method in accordance with claim 13 characterized in that the erosion liquid in the channel is replaced by a flusher apparatus with a speed in the channel of 100 to 400 mm/s.

15. A method in accordance with claim 13 characterized by, for rotationally symmetric implants such as hip joint shells for example, rotating the implant in the liquid about its axis of rotation, while covering only a part of the surface of the implant to be processed with the electrode.

16. A method in accordance with claim 1 characterized in that, for the improved regulation of the current density in the electrolyte, its temperature is held constant to a certain extent, for a cooking salt solution at a temperature <90° C.

17. A method for producing a surface on a metallic part which has a coarse structure of elevations in the form of ribs and of depressions in the form of grooves with a width of 2 mm to 0.4 mm comprising in a first step, coating the metallic surface with an adhering, electrochemically effective protective lacquer layer which can be removed by means of a laser of a selected wavelength at a sufficiently low energy density that a significant energy threshold exists with respect to the energy density required for an ablation of the metal to prevent an ablation of the metal, in a further step, inscribing furrows into the protective lacquer with the laser corresponding to centerlines of envisaged grooves, a width of the furrows amounting to only a fraction of the widths of the envisaged grooves, in a further step, exposing the surface provided with furrows in the protective lacquer to an electrically conductive fluid to form the grooves which simultaneously grow in depth and in width parallel to the surface in a region of the furrows by means of electrochemical erosion and/or etching for a limited time, and in a further step, removing the remaining protective lacquer.

* * * * *

UNITED STATES PATENT AND TRADEMARK OFFICE
CERTIFICATE OF CORRECTION

PATENT NO.   : 5,965,006
DATED        : October 12, 1999
INVENTOR(S)  : ROLAND BAEGE, et al.

It is certified that error appears in the above-identified patent and that said Letters Patent is hereby corrected as shown below:

On the face sheet, under [73] Assignee:, change "Sweden" to --Switzerland --

Signed and Sealed this

Third Day of April, 2001

*Attest:*

NICHOLAS P. GODICI

*Attesting Officer*      *Acting Director of the United States Patent and Trademark Office*